United States Patent [19]

Willmund et al.

[11] 4,451,261

[45] May 29, 1984

[54] PREPARATION OF LUBRICATING AGENTS FOR LEATHERS AND FURS

[75] Inventors: Wolf-Dieter Willmund, Düsseldorf; Manfred Biermann, Mühlheim; Horst Baumann, Leichlingen; Hans-Herbert Friese, Monheim; Friedrich Pieper, Langenfeld, all of Fed. Rep. of Germany

[73] Assignee: Henkel KGaA, Duesseldorf, Fed. Rep. of Germany

[21] Appl. No.: 481,636

[22] Filed: Apr. 4, 1983

[30] Foreign Application Priority Data

Oct. 20, 1982 [DE] Fed. Rep. of Germany ....... 3238741

[51] Int. Cl.$^3$ ............................................... C14C 9/02
[52] U.S. Cl. ..................................... 8/94.22; 8/94.23; 252/8.57
[58] Field of Search .............. 252/8.57; 8/94.22, 94.23

[56] References Cited

U.S. PATENT DOCUMENTS 3,724,999  4/1973  Stein et al. ........................... 252/8.57
3,765,833  10/1973  Plapper et al. ....................... 252/8.57
3,988,247  10/1976  Dieckelmann et al. .............. 8/94.22

FOREIGN PATENT DOCUMENTS 2031167  11/1970  France ................................ 252/8.57

Primary Examiner—Maria Parrish Tungol
Attorney, Agent, or Firm—Ernest G. Szoke; Nelson Littell, Jr.

[57] ABSTRACT

This invention relates to a process for preparing sulfonated lubricating agents for leather and tanned furs consisting of the steps of:

(a) chlorinating natural or synthetic higher fatty acids or esters of higher fatty acids having chain lengths of from 8 to 24 carbon atoms containing olefinically unsaturated fractions, up to saturation of the double bonds;

(b) sulfochlorinating the chlorinated product from step (a) with chlorine and $SO_2$ at a temperature of from about 20° to 90° C., optionally under UV-radiation, for a time sufficient to obtain a compound having a chlorine content of from about 5 to 30 percent by weight and a content of $SO_2Cl$ groups of from about 1 to 20 percent by weight, the ratio of chlorine atoms to $SO_2Cl$ groups being from about 0.7:1 to 70:1; and (c) saponifying the product from step (b) to form a water-emulsifiable alkali metal, ammonium, or lower alkyl-ammonium salt of the product of step (b).

14 Claims, No Drawings

4,451,261

PREPARATION OF LUBRICATING AGENTS FOR LEATHERS AND FURS

FIELD OF THE INVENTION

This invention relates to lubricating agents for leather and furs. More specifically, this invention relates to sulfonated chlorination products for the fat-liquoring of leathers and furs and to the preparation thereof.

BACKGROUND OF THE INVENTION

U.S. Pat. No. 3,988,247, incorporated herein by reference, discloses fat-liquoring, or lubricating, agents for leathers or furs based upon sulfonated chlorination products of natural or synthetic higher fatty acids or esters of fatty acids in the form of their alkali metal, ammonium, or amine salts. These agents consist of those sulfonated chlorination products that were obtained by chlorinating higher fatty acids or esters of higher fatty acids having chain lengths of from 8 to 24 carbon atoms up to a chlorine content of from about 20 to 45 percent by weight, the products of chlorination generally not containing any olefinic double bonds, and subsequently sulfonating said products with $SO_3$ to attain an $SO_3$ content of from 50 to 100 mol percent, based upon the products of chlorination.

In addition, co-pending U.S. patent application Ser. No. 259,526, filed May 1, 1981, incorporated herein by reference, describes lubricating agents for leather or furs based upon sulfonated chlorination products of natural or synthetic higher fatty acids or fatty acid esters in the form of their alkali metal, ammonium, or amine salts. These lubricating agents are characterized in that they essentially consist of sulfonated chlorination products of the type obtained by the sulfochlorination of higher fatty acids or of esters of higher fatty acids having chain lengths of from 8 to 24 carbon atoms with chlorine and $SO_2$, optionally in the presence of UV-radiation, at a temperature in the range of from about 20° to 90° C. up to a content of bound chlorine of from 5 to 30 percent by weight and a content of $SO_2Cl$ groups of from about 1 to 20 percent by weight, the ratio of chlorine atoms to $SO_2Cl$ groups being from about 0.7:1 to 70:1, followed by saponification.

OBJECTS OF THE INVENTION

It is an object of the invention to provide an improved procedure for preparing fat-liquoring agents for leathers or furs.

It is also an object of the invention to provide a process for the production of a sulfonated lubricating agent for leather and tanned furs from higher fatty acids or esters of higher fatty acids having chain lengths of from 8 to 24 carbon atoms containing unsaturated fractions by (a) chlorination up to saturation of the double bonds; (b) sulfochlorination with chlorine and $SO_2$ at a temperature of from about 20° to 90° C., optionally under UV-radiation, for a time sufficient to attain a chlorine content of from about 5 to 30 percent by weight and a content of $SO_2Cl$ groups of from about 1 to 20 percent by weight, the ratio of chlorine atoms to $SO_2Cl$ groups being from about 0.7:1 to 70:1; and (c) saponification.

These and other objects of the invention will become more apparent from the discussion below.

DETAILED DESCRIPTION OF THE INVENTION

It has now been found that the known processes for producing lubricating agents of the type in question may be further improved provided that the sulfonated chlorination products are produced from higher fatty acid or fatty acid ester mixtures containing unsaturated fractions. In this instance, the first step comprises chlorination up to saturation of the double bonds, followed by sulfochlorination with chlorine and $SO_2$. Subsequent saponification gives the required lubricating agents.

Accordingly, the present invention relates to lubricating agents for leather and furs based upon sulfonated chlorination products of natural or synthetic higher fatty acids or fatty acid esters in the form of their alkali metal, ammonium, or amine salts, characterized in that they consist essentially of sulfonated chlorination products of the type obtained from higher fatty acids or esters of higher fatty acids (chain lengths of from 8 to 24 carbon atoms) containing unsaturated fractions by (a) chlorination up to saturation of the double bonds, (b) subsequent sulfochlorination with chlorine and $SO_2$, optionally in the presence of UV-radiation, at from about 20° to 90° C. up to a content of bound chlorine of from about 5 to 30 percent by weight and a content of $SO_2Cl$ groups of from about 1 to 20 percent by weight, the ratio of chlorine atoms to $SO_2Cl$ groups amounting to from about 0.7:1 to 70:1, followed by (c) saponification. The present invention also relates to a process for producing these lubricating agents under the above-mentioned conditions. The new process leads to better utilization of the gases used, i.e., to smaller losses of $Cl_2$ and $SO_2$ in the waste gas, and hence to a higher degree of sulfonation of the fats used and to a lower consumption of chlorine and $SO_2$.

To produce the lubricants of the invention, it is preferred to start with higher fatty acids or esters of higher fatty acids having from 8 to 24, preferably 10 to 20, carbon atoms and having iodine numbers of from 10 to 120. Mixtures of fatty acids of naturally occurring fats or oils, especially those with a share of singly or repeatedly unsaturated fatty acids, are preferred. Examples of such fatty acid mixtures include mixtures obtained from coconut oil, soybean oil, palm kernel oil, cottonseed oil, rapeseed oil, linseed oil, castor oil, sunflower seed oil, olive oil, neat's foot oil, peanut oil, herring oil, cod liver oil, shark liver oil, whale oil, tallow fat, and lard. Furthermore, the fatty acid mixtures obtained form these fats or oils and naturally occurring wax esters, such as sperm oil, may be used as starting material for the production of lubricating agents. In such a case, however, the chlorination or sulfochlorination reaction is frequently impeded by the high viscosity of the corresponding products.

Particularly preferred starting materials for producing the lubricating agents comprise synthetic esters of mixtures of saturated and unsaturated fatty acids having from 8 to 24, preferably from 10 to 20, carbon atoms and having iodine numbers of from 10 to 120, as, for example, commercially prepared decanecarboxylic acid, palmitic acid, or stearic acid still containing acids having residual double bonds, or dodecenecarboxylic acid, oleic acid, linoleic acid, or carboxylic acids produced by the oxidation of paraffin with monohydric aliphatic alcohols having from 1 to 4 carbon atoms, such as methanol, ethanol, isopropanol, or butanol. Because of their ready availability, the fatty acid esters obtained from natural animal or vegetable fats, oils, or waxes by transesterification with lower monohydric aliphatic alcohols, particularly methanol, are preferred. Finally, it is also possible to use esterification products of the above-mentioned fatty acids and polyhydric aliphatic alcohols having from 2 to 6 carbon atoms, such as ethyleneglycol, 1,2-propyleneglycol, glycerin, pentaerythrite, or sorbitol, or higher alcohols having from 8 to 24 carbon atoms, such as decylalcohol or oleylalcohol.

The above-mentioned starting materials are (a) first chlorinated in known manner at relatively low temperatures, the quantity of chlorine to be introduced being measured in such a way that it is sufficient to saturate the olefinic fraction of the starting materials by additive chlorination. The chlorination reaction is carried out at temperatures of up to at most about 30° C. and preferably at temperatures in the range of from about 20° to 25° C. in the absence of actinic light. In step (b) of the process, sulfochlorination is carried out by the simultaneous introduction of $Cl_2$ and $SO_2$ at a molar ratio of from 60:1 to 1.4:1. The reaction temperature is in the range of from about 20° to 90° C. and, if necessary, is maintained at the desired level by cooling. A reaction temperature in the range from about 40° to 75° C. is preferred. The reaction is promoted by irradiation with UV-light (mercury vapor lamp). The reaction is complete after about 2 to 10 hours, after which time from about 5 to 30 percent by weight of chlorine and from about 1 to 20 percent by weight of $SO_2Cl$ groups have been added. The ratio of chlorine atoms to $SO_2Cl$ groups is in the range of from about 0.7:1 to 70:1, preferably in the range of from about 2:1 to 20:1, more preferably in the range of from about 3:1 to 7:1.

Subsequent saponification is performed with aqueous, approximately 30% sodium or potassium hydroxide solution at approximately 50° C., neutralization being carried out with an excess of the same alkali metal hydroxides, ammonia solution, an aliphatic or cycloaliphatic amine, or an alkanolamine having from 2 to 6 carbon atoms, such as triethanolamine. Liquid, highly concentrated products that can be emulsified in water and have an excellent fastness to oxidation, light, and acid are obtained, which are eminently suitable for the lubrication or fat-liquoring of light-colored, pastel-tinted, and white leathers as well as for the fat-liquoring of valuable and delicate furs.

If dark-colored or more unsaturated raw materials are used, bleaching of the sulfonation products may be advisable. This is accomplished in the usual manner by adding small quantities of from approximately 0.5 to 5%, preferably from 1 to 4%, $H_2O_2$ solutions to the acid sulfonation product at temperatures of from about 20° and 80° C., preferably from about 40° and 60° C. In this way, it is possible to lighten even dark-colored sulfonation products very considerably.

The products are used in the usual manner in the form of aqueous emulsions for the fat-liquoring of leather or for the treatment of furs. Preferably the sulfonated lubricants of the invention are applied to the leather and furs by treating the leather in vats at a temperature of from about 40° to 80° C., preferably about 60° C., with a float or aqueous liquor of from about 80 to 250 percent, preferably from about 100 to 120 percent, containing from about 3 to 10 percent of the sulfonated lubricants of the invention, both based upon the amount of the leather or furs being treated.

The products of the invention are self-emulsifying so that the supplemental addition of emulsifiers is generally not required. However, to achieve specific effects, the sulfonation products may be combined with the corresponding non-sulfonated chlorination products or other conventional leather treatment agents, such as non-sulfonated oils or fats, for example, fish oil, sperm oil, neat's foot oil, and the like, or synthetic lubricants such as chloroparaffins, paraffin sulfonates, sulfated natural fats or oils, synthetic fatty acid esters, or mineral oils or the like, optionally in conjunction with anionic, non ionic, or cationic emulsifiers, preferably non-ionic surface-active compounds, such as ethylene oxide addition products to higher fatty alcohols, alkylphenols, or fatty amines having a chain length of from 10 to 20 carbon atoms. Stabilization of the products may be accomplished by neutralizing any hydrogen chloride residues still present or newly formed by means of epoxide compounds in amounts of from about 0.5 to 5 percent by weight. Pertinent examples include the following: glycide, epichlorohydrin, glycidyl ethers of monohydric or polyhydric alcohols, such as glycol, glycerin, or sorbitol, as well as epoxidized fats such as epoxidized soybean oil, linseed oil, or oleic acid butyl ester.

The products are well absorbed by the leather and yield excellent lubricating and softening action, with a remarkable resistance to water and aqueous or organic detergent solutions. Their tendency to migrate under thermal stress is minimal so that fusing operations or the vulcanization of rubber soles to shoe uppers can be carried out without difficulties. The good light, oxidation, and acid resistance of the sulfonated products of the invention, which also makes them suitable for the lubrication of sensitive and light-colored leathers and furs, is to be particularly emphasized. The treated leather or furs are characterized by their feeling especially pleasantly soft and oiled to the touch and by a beautiful glossiness of the fur.

The examples below are intended to illustrate the invention and should not be construed as limiting the invention thereto. The sulfochlorination reactions described in the examples were carried out in the following manner:

A glass reactor column filled with Raschig rings and enclosed by a double-jacket for heating and cooling liquid stood atop a 2 liter round-bottom flask having a bottom drain. The starting material was pumped through the bottom drain of the flask and then through a heatable rising tube into the head of the reaction column by means of a hose pump. The gases, chlorine and sulfur dioxide, were introduced through needle valves at the lower end of the column. Rotameters were used for the metering. The flow rate of the gases was from about 25 to 120 liters/hr for the chlorine and from about 4 to 50 liters/hr for the $SO_2$. The HCl gas produced was drawn off together with the rest of the unreacted starting gases through a washing bottle system at the head of the reaction column. The glass reaction column was irradiated from the outside with a mercury vapor lamp.

EXAMPLES

Example 1

One kilogram of tallow fatty acid methyl ester ($C_{16}$–$C_{18}$; iodine number=53) were initially introduced into the reactor and reacted with 50 liters of chlorine for one hour at 25° C. After heating to 50° C., 50 liters/hr of chlorine and 12.5 liters/hr of $SO_2$ were introduced in the presence of light from a mercury vapor lamp. The contents of the flask were circulated during the reaction by means of a peristaltic pump.

The reaction was terminated after three hours, and the reaction product (1399 gm) was freed in vacuo from the dissolved gases (mainly HCl). The reaction product contained 22.85 percent by weight of bound chlorine and 8.90 percent by weight of bound $SO_2Cl$. The iodine number was below 1. The waste gas collected in dilute NaOH consisted of 193.1 gm of HCl, 8.54 gm of $SO_2$, and 0.6 gm of $Cl_2$.

Saponification and neutralization were carried out with 300 gm of aqueous 30% NaOH at temperatures in the range from 40° to 50° C., resulting in the formation of a stable emulsion which contained approximately 40 percent by weight of chlorinated tallow fatty acid methyl ester sulfonate, 42 percent by weight of chlorinated tallow fatty acid methyl ester, and 18 percent by weight of inorganic salts and water.

Example 2

An amount of 17.25 kg of tallow fatty acid methyl ester was initially introduced into a similar, but larger recirculation apparatus of the type used in Example 1 and heated to 25° C., and 1000 liters of chlorine were introduced over a period of one hour, during which the temperature was kept at 25° C. The reaction mixture was then heated to 50° C., and 500 liters/hr of chlorine and 150 liters/hr of $SO_2$ were introduced over a period of four hours in the presence of light from a mercury vapor lamp. The reaction was accompanied by the evolution of HCl, which was removed and collected in dilute NaOH.

Upon termination of the sulfochlorination reaction, the product was degassed in vacuo. The yield amounted to 23.7 kg of chlorinated tallow fatty acid methyl ester sulfonate containing 20.85 percent by weight of bound chlorine and 10.50 percent by weight of bound $SO_2Cl$ (iodine number = <1). The waste gas contained 3.0 kg of HCl, 0.2 kg of $SO_2$, and 0.0 kg of chlorine.

Next, 1151 gm of the reaction product were hydrolyzed and neutralized with 268 gm of a 31% sodium hydroxide solution. The homogenized product contained approximately 50 percent by weight of chlorinated tallow fatty acid methyl ester sulfonate, 30 percent by weight of chlorinated tallow fatty acid methyl ester, and 20 percent by weight of inorganic salts and water. The product could be diluted with water to form a stable emulsion.

Comparison Example 2A

A comparison example corresponding to Example 2 was carried out using the same quantity of tallow fatty acid methyl ester, a gas mixture (750 liter/hr of chlorine and 150 liters/hr of $SO_2$) being introduced simultaneously and uniformly over a period of four hours at 50° C. The result was 22.9 kg of chlorinated tallow fatty acid methyl ester sulfonate containing 20.85 percent by weight of bound chlorine and 7.70 percent by weight of bound $SO_2Cl$ (iodine number = <1). The waste gas contained 2.67 kg of HCl, 0.67 kg of $SO_2$, and 0.74 kg of $Cl_2$.

Example 3

A quantity of 17.25 kg of coconut oil fatty acid methyl ester last runnings ($C_{16}$–$C_{18}$; iodine number = 52) was chlorinated and sulfochlorinated in the same apparatus and under the same conditions as in Example 2. A total of 3000 liters of chlorine and 600 liters of $SO_2$ was consumed. The end product obtained, in a yield of 23.5 kg, was chlorinated coconut oil fatty acid methyl ester sulfonate containing 20.7 percent by weight of bound chlorine and 8.70 percent by weight of bound $SO_2Cl$ (iodine number = <1). The waste gas contained 2.6 kg of HCl, 0.39 kg of $SO_2$, and 0.41 kg of $Cl_2$.

Example 4

Shoe upper leathers retanned with synthetic or vegetable tannins or resin tannins or with a combination thereof were fat-liquored for 45 minutes at 60° C. with from 100 to 120 percent by weight of liquor and from 5 to 6 percent by weight of the sulfochlorination product of Example 2 as the fat-liquoring substance, based upon the weight of the leathers. The leathers, dried and finished in the usual way, were distinguished by a soft, supple, and compact feel, high grain strength, and excellent stability to light and oxidation.

Example 5

Chrome-tanned and dyed clothing leathers were fat-liquored for 45 minutes at 60° C. with from 100 to 120 percent by weight of liquor and from 7 to 10 percent by weight of fat-liquoring substance consisting of a mixture of 80 percent by weight of the sulfochlorination product of Example 1 and 20 percent by weight of a corresponding non-sulfonated chlorinated tallow fatty acid methyl ester. The leathers, dried and finished in the usual way, were distinguished by a soft, supple, and compact feel and by excellent stability to light and oxidation.

Example 6

Pastel-tinted, chrome-tanned glove leather of lambskin was fat-liquored for 45 minutes at 60° C. with 100 percent by weight of liquor and from 6 to 8 percent by weight of fat-liquoring substance consisting of a mixture of 75 percent by weight of the sulfochlorination product of Example 3, 21 percent by weight of a non-sulfonated chlorinated coconut oil fatty acid methyl ester, and 4 percent by weight of a tallow amine reacted with 4 mols of ethylene oxide, followed by drying and finishing in the usual way. The leather was distinguished by a pliable, flexible, and soft feel and by good light-fastness.

Example 7

Cowhides pickled in the usual way were tanned with 8 percent by weight of a standard commercial chrome-tanning liquor ($Cr_2O_3$ content of 25 percent by weight based upon 100 percent by weight of liquor) and pre-liquored in the same bath with 2 percent by weight of the fat-liquoring substance consisting of a mixture of 95 percent by weight of sulfochlorination product of Example 1 and 5 percent by weight of a tallow alcohol reacted with 20 mols of ethylene oxide. These furniture leathers, retanned in the usual way, dyed, and then relubricated with 9 to 10 percent by weight of the sulfochlorination product and dried, were distinguished by a supple, soft feel and good light-fastness.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the preparation of sulfonated lubricating agents for leather and tanned furs consisting of the steps of:
   (a) chlorinating natural or synthetic higher fatty acids or esters of higher fatty acids having chain lengths of from 8 to 24 carbon atoms containing olefinically unsaturated fractions, up to saturation of the double bonds;
   (b) sulfochlorinating the chlorinated product from step (a) with chlorine and $SO_2$ at a temperature of from about 20° to 90° C., optionally under UV-radiation, for a time sufficient to obtain a compound having a chlorine content of from about 5 to 30 percent by weight and a content of $SO_2Cl$ groups of from about 1 to 20 percent by weight, the ratio of chlorine atoms to $SO_2Cl$ groups being from about 0.7:1 to 70:1; and
   (c) saponifying the product from step (b) to form a water-emulsifiable alkali metal, ammonium, or lower alkyl-ammonium salt of the product of step (b).

2. The process of claim 1, wherein the fatty acids in step (a) are fatty acids of naturally occurring fats or oils having chain lengths of 10 to 20 carbon atoms and iodine numbers of from 10 to 120.

3. The process of claim 1, wherein the esters of fatty acids in step (a) are methyl esters of fatty acids having chain lengths of from 10 to 20 carbon atoms and iodine numbers of from 10 to 120.

4. The process of claim 1, wherein in step (b) the ratio of chlorine atoms to $SO_2Cl$ groups is from about 2:1 to 20:1.

5. The process of claim 4, wherein the ratio is from about 3:1 to 7:1.

6. The process of claim 1, wherein the combination of steps (a) and (b) results in smaller losses of chlorine and $SO_2$ as compared to a process where step (a) is omitted.

7. A sulfonated lubricating agent for leather and tanned furs prepared according to claim 1.

8. The lubricating agent of claim 7 which also contains non-sulfonated chlorination products.

9. The lubricating agent of claim 7 which also contains conventional leather processing products selected from the group consisting of the oils, fats, chloroparaffins, paraffin sulfonates, sulfated natural fats or oils, synthetic fatty acid esters, and mineral oils, and mixtures thereof.

10. The lubricating agent of claim 7 which also contains one or more anionic, nonionic, or cationic emulsifying agents.

11. The lubricating agent of claim 10, wherein the nonionic emulsifying agents comprise ethylene oxide adducts with higher fatty alcohols, alkylphenols, or fatty amines having chain lengths of from 80 to 20 carbon atoms.

12. The lubricating agent of claim 7 which also contains from about 0.5 to 5 percent by weight of an epoxide compound that has a stabilizing effect.

13. A process for lubricating leathers or tanned furs which comprises treating said leathers or tanned furs with an effective amount of the lubricating agent of claim 7.

14. The process of claim 13, wherein the lubricating agent is in the form of a stable emulsion.

* * * * *